United States Patent
Jansson et al.

(10) Patent No.: US 9,572,920 B2
(45) Date of Patent: Feb. 21, 2017

(54) DISPOSABLES FOR BLOOD TREATMENT, AND METHODS OF OPERATING THE SAME

(75) Inventors: Olof Jansson, Vellinge (SE); Mattias Holmer, Lund (SE); Eddie Nilsson, Hoor (SE); Lennart Jonsson, Bjarred (SE)

(73) Assignee: Gambro Lundia AB, Lund (SE)

( * ) Notice: Subject to any disclaimer, the term of this patent is extended or adjusted under 35 U.S.C. 154(b) by 399 days.

(21) Appl. No.: 14/129,097

(22) PCT Filed: Jun. 18, 2012

(86) PCT No.: PCT/EP2012/061551
§ 371 (c)(1),
(2), (4) Date: Mar. 12, 2014

(87) PCT Pub. No.: WO2012/175435
PCT Pub. Date: Dec. 27, 2012

(65) Prior Publication Data
US 2014/0174542 A1   Jun. 26, 2014

Related U.S. Application Data

(60) Provisional application No. 61/499,241, filed on Jun. 21, 2011.

(30) Foreign Application Priority Data

Jun. 21, 2011 (SE) ...................... 1150571

(51) Int. Cl.
*A61M 1/36* (2006.01)
*A61M 1/30* (2006.01)

(52) U.S. Cl.
CPC .............. *A61M 1/367* (2013.01); *A61M 1/30* (2013.01); *A61M 1/302* (2014.02); *A61M 1/303* (2014.02);
(Continued)

(58) Field of Classification Search
CPC ...... A61M 1/30; A61M 1/3621; A61M 1/367; A61M 2205/125; A61M 2205/128; Y10T 137/0318; Y10T 137/85986; Y10T 137/86035
See application file for complete search history.

(56) References Cited

U.S. PATENT DOCUMENTS

| | | | |
|---|---|---|---|
| 6,645,166 B2 | 11/2003 | Scheunert et al. | |
| 2002/0041825 A1 | 4/2002 | Scheunert et al. | |

(Continued)

FOREIGN PATENT DOCUMENTS

| | | |
|---|---|---|
| DE | 33 28 744 A1 | 2/1985 |
| DE | 10 2005 001779 A1 | 9/2006 |

(Continued)

OTHER PUBLICATIONS

Thompson-Medical, "Renal Solutions—Blood Pump," downloaded from www.t-med.co.uk/dialysis/renalsolutions-bloodpump.htm May 18, 2011.

*Primary Examiner* — Jaqueline Stephens
*Assistant Examiner* — Benjamin Klein
(74) *Attorney, Agent, or Firm* — K&L Gates LLP

(57) ABSTRACT

A disposable for use in blood treatment including a blood treatment unit and two membrane pumps connected in parallel on one side of the blood treatment unit. The disposable is operable in a single-needle mode, in which the pumps generate a pulsatile flow of blood through the blood treatment unit, and in a double-needle mode, in which the pumps generate an essentially continuous flow of blood through the blood treatment unit. The pumps connect to a supply of treatment fluid such that alternating flows of treatment fluid causes the pumps to generate the desired flows of blood in the single-needle and double-needle modes. The treatment fluid may be used as motive fluid for displacing the blood in the membrane pumps and/or as (Continued)

control fluid for controlling opening and/or closing of upstream and downstream commutation valves in the membrane pumps.

13 Claims, 6 Drawing Sheets

(52) U.S. Cl.
CPC ............ *A61M 1/306* (2014.02); *A61M 1/3621* (2013.01); *A61M 2205/125* (2013.01); *A61M 2205/128* (2013.01); *Y10T 137/0318* (2015.04); *Y10T 137/85986* (2015.04); *Y10T 137/86035* (2015.04)

(56) References Cited

U.S. PATENT DOCUMENTS

| | | | |
|---|---|---|---|
| 2009/0008306 A1 | 1/2009 | Cicchello et al. | |
| 2009/0008331 A1* | 1/2009 | Wilt .................. | A61M 1/16 210/647 |
| 2009/0012448 A1 | 1/2009 | Childers et al. | |
| 2009/0099498 A1 | 4/2009 | Demers et al. | |
| 2009/0137940 A1 | 5/2009 | Orr | |
| 2010/0241062 A1 | 9/2010 | Morris et al. | |

FOREIGN PATENT DOCUMENTS

| | | | | |
|---|---|---|---|---|
| SE | WO 2009127624 A2 * | 10/2009 | ............ | A61M 1/106 |
| WO | 2009127624 A2 | 10/2009 | | |
| WO | 2009127627 A1 | 10/2009 | | |

* cited by examiner

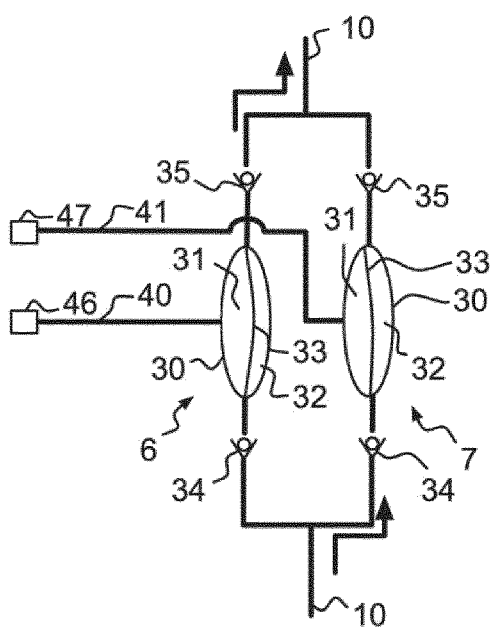
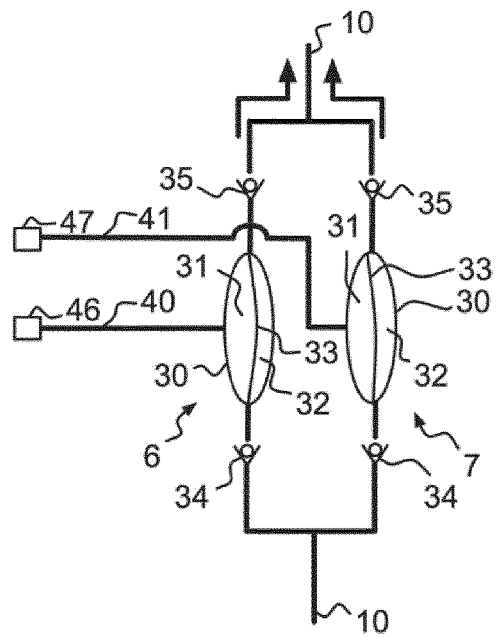
FIG. 11A  FIG. 11B
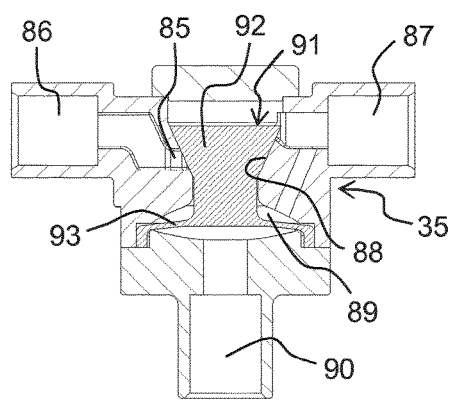
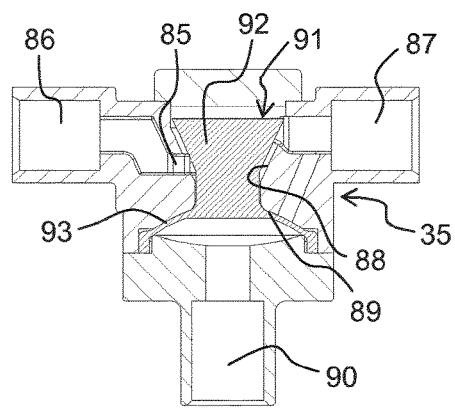
FIG. 12A  FIG. 12B

DISPOSABLES FOR BLOOD TREATMENT, AND METHODS OF OPERATING THE SAME

CROSS RELATED APPLICATION

This application is the U.S. national phase of International Application No. PCT/EP2012/061551 filed 18 Jun. 2012 which designated the U.S. and claims priority to Swedish Patent Application No. 1150571-6 filed 21 Jun. 2011 and U.S. Provisional Patent Application No. 61/499,241 filed 21 Jun. 2011, the entire contents these applications are incorporated by reference.

TECHNICAL FIELD

The present invention relates to disposables that contain blood lines, a blood pump and a blood treatment unit and are intended for inclusion in a blood treatment apparatus, such as a hemodialysis machine. In particular, the present invention relates to techniques for controlling the operation of such disposables.

BACKGROUND ART

Today, various methods for hemodialysis are known, which include so-called double-needle or dual-needle (DN) dialysis and single-needle (SN) dialysis.

In DN dialysis, blood is withdrawn from a patient via one access device (e.g. a needle or catheter), and returned to the patient via another access device (e.g. a needle or catheter). A DN dialysis system is typically configured to generate a steady flow of blood from and to the patient, and to pump the blood continuously through the dialyzer.

In SN dialysis, one and the same access device (e.g. needle or catheter) is used for withdrawing and returning blood, which may be advantageous in a self-care setting since there is little risk of significant blood loss if the access device is accidentally dislodged from the patient. Also, when using SN dialysis, fewer needle punctures for accessing the patient's blood are required compared to DN dialysis. However, since SN dialysis withdraws and returns blood cyclically via one and the same access device, more time may be required for completing a dialysis treatment in comparison with DN dialysis.

Accordingly, DN dialysis has both advantages and disadvantages in comparison with SN dialysis, and vice versa. For this reason, it is desirable to offer blood treatment devices and dialysis machines that allow both DN and SN operation.

For home dialysis, as well as for dialysis in a clinical setting, it may be desirable to provide part of the dialysis system as a disposable which is designed to be attached to a dialysis machine. For ease of use and patient safety, such a disposable may comprise the extracorporeal blood circuit, including blood lines, connectors for access device(s), a dialyzer and a blood pump. At the start of a treatment, in such a scenario, the disposable may be connected to a dialysis machine so as to receive appropriately conditioned dialysis fluid and to be controlled to circulate the dialysis fluid through the dialyzer. After completed treatment, the disposable may be disconnected from the dialysis machine and discarded.

U.S. Pat. No. 6,645,166 discloses a disposable kit that permits both SN and DN operation when connected to a dialysis machine. The disposable kit comprises a dialyzer with an inlet connected to a feed line and an outlet connected to a return line. The feed line comprises two parallel line branches, each having a membrane pump. Each membrane pump comprises a pressure chamber, which is controlled to expand or compress by being alternately filled and emptied of a gas or a liquid, and electromagnetically or pneumatically actuated control valves on both sides of the pressure chamber to control the direction of the blood flow generated by the pressure chamber. For DN operation, the feed and return lines are connected to different access devices, and for SN operation, the feed and return lines are connected to a common access device. A connection line is arranged to extend between the outlet of the dialyzer and one of the membrane pumps and is provided with a control valve which is controlled to open or close to ensure a continuous flow of blood through the dialyzer in both DN and SN operation. Such a disposable kit requires use of a special dialysis machine, which has a dedicated system for alternately filling and emptying the pressure chamber with gas/liquid. It also requires the dialysis machine to provide proper control signals for the control valves. Still further, the disposable defines relatively complicated blood flow paths, which may lead to in an elevated risk for clogging, blood leakage and/or hemolysis.

The prior art also comprises US2009/0137940, which discloses a double diaphragm pump for application as a single use disposable medical blood pump, e.g. in dialysis systems. The pump comprises two pump chambers connected in parallel, where each pump chamber contains a flexible chamber diaphragm for pumping blood. An inlet valve and an outlet valve, in the form of diaphragm valves, are arranged on either side of each pump chamber. The operation of the pump is controlled by selectively applying vacuum or pneumatic pressure to the chamber diaphragm and the diaphragm valves. The pump is suggested for use in a dual-needle hemodialysis system, e.g. to generate a substantially constant blood flow from the patient to the extracorporeal circuit and/or from extracorporeal circuit to the patient, or to provide a pulsatile blood flow to the dialyzer downstream of the pump in the extracorporeal circuit and essentially constant blood flow from the patient to the extracorporeal circuit.

A similar pump, denoted PULSAR™ Blood Movement System, is described in "Renal Solutions™—Blood Pump", located at http://www.t-med.co.uk/dialysis/renalsolutions-bloodpump.htm. This pump consists of two chambers with a flexible medial diaphragm in each chamber. The top and bottom of each chamber opens to bloodlines; the back is attached to a pneumatic system, which is used to move the diaphragm. During dialysis, clamps below the chambers open and a vacuum is used to draw the diaphragm to the side of each chamber, which pulls blood into the chambers. The lower clamps then close, the upper clamps (between pump and dialyzer inlet) open, and positive pressure applied to the diaphragm pushes the blood from the chamber and towards the dialyzer. The chambers fill and empty in unison for SN dialysis and alternate, one filling while the other empties, in DN operation. It is stated that the pump is part of the arterial bloodline and designed as a single-use disposable. Such a disposable may operate with simple blood flow paths, but needs a special dialysis machine containing a pneumatic system for generating alternating positive and negative pressures within the pump chambers. The dialysis machine must also be provided with adequately controlled clamps.

US2010/0241062 discloses a medical fluid pump system comprising reciprocating piston heads which are attached to a membrane that defines a pair of fluid pump chambers. Thereby, the pump system contains a pair of mechanically actuated membrane pumps. The movement of fluid into and out of the fluid pump chambers is controlled by selectively inflating and deflating inflatable members, which thereby are brought into and out of contact with depressible dome regions in flow channels extending to the fluid pump chambers.

The prior art also comprises WO2009/127627, which aims at eliminating the need for pressure sensors in the blood lines of the extracorporeal circuit in a dialysis system. This is achieved by arranging one or more membrane pumps as blood pumps in the extracorporeal circuit, and using the dialysis fluid as working medium of the membrane pump, whereby the pressure of the dialysis fluid may be monitored for measuring the pressure of the blood in the extracorporeal circuit.

SUMMARY

It is an object of the invention to at least partly overcome one or more of the above-identified limitations of the prior art.

One objective is to provide a disposable capable of being used in both SN and DN dialysis, with minimum modification of the disposable.

Another objective is to provide a disposable that has a low risk of malfunctions such as leakage, clogging, activation of blood and hemolysis.

Yet another objective is to provide a disposable that may be included in a blood treatment apparatus with a design similar to conventional blood treatment apparatuses.

One or more of these objects, as well as further objects that may appear from the description below, are at least partly achieved by means of disposables, methods of operating disposables, and an apparatus for blood treatment according to the independent claims, embodiments thereof being defined by the dependent claims.

A first aspect of the invention is a disposable for use in blood treatment. The disposable comprises: a blood treatment unit for connection to a supply system operable to pump a treatment fluid through the blood treatment unit during the blood treatment, a blood withdrawal connector which is connected to the blood treatment unit via a blood withdrawal line, and a blood return connector which is connected to the blood treatment unit via a blood return line. One of the blood withdrawal and blood return lines comprises a membrane pump arrangement operable to pump blood through the blood treatment unit. The membrane pump arrangement comprises first and second blood line branches that are connected at an upstream end and at a downstream end. A first membrane pump is arranged in the first blood line branch, and a second membrane pump is arranged in the second blood line branch. Each of the first and second membrane pumps comprises a pumping chamber and a flexible member separating the pumping chamber into a blood compartment and a working fluid compartment and being movable within the pumping chamber so as to vary the volume relationship between the blood compartment and the working fluid compartment. The blood compartment is arranged for fluid communication with the upstream and downstream ends, and the working fluid compartment is arranged for fluid communication with the supply system. Each of the first and second membrane pumps comprises an upstream valve and a downstream valve for controlling blood flow between the blood compartment and the upstream end and the downstream end, respectively. The disposable is configurable for operation in a first blood access mode, in which the blood withdrawal and blood return connectors are connected to a single access device, and the membrane pump arrangement is operable to alternately draw blood from the upstream end, and to pump blood through the downstream end, thereby generating a pulsatile flow of blood through the blood treatment unit. The disposable is also configurable for operation in a second blood access mode, in which the blood withdrawal and blood return connectors are connected to a first and a second access device, respectively, and the membrane pump arrangement is operable to concurrently draw blood from the upstream end and pump blood through the downstream end, thereby generating an essentially continuous flow of blood through the blood treatment unit. The membrane pump arrangement is configured for connection to the supply system such that alternating flows of treatment fluid generated by the supply system and supplied to the first and second membrane pumps causes the membrane pump arrangement to generate the pulsatile flow of blood in the first mode and the essentially continuous flow of blood in the second mode.

The disposable according to the first aspect provides a number of technical advantages. The provision of a membrane pump arrangement that comprises a first and a second membrane pump connected in parallel on one side of the blood treatment unit, with each of the membrane pumps being operable to alternate (or "commutate") between a first phase for drawing blood from the upstream end, and a second phase for pumping blood towards the downstream end, may facilitate the task of timing the commutation between the membrane pumps. Timing may be facilitated since both membrane pumps are exposed to the same pressure levels in the blood. Thereby, little or no balancing of the blood flows to/from the membrane pumps is needed.

The disposable may be switched between the first and second blood access modes by changing the timing of commutation between the pumps. For example, in the second blood access mode, the first and second membrane pumps may be operated with essentially opposite first and second phases. In the first blood access mode, the first and second membrane pumps may be operated with essentially concurrent first and second phases. Alternatively, in the first blood access mode, only the second membrane pump may be operated while communication of blood between the first and second blood line branches is prevented.

By allowing the disposable to generate a pulsatile flow of blood through the blood treatment unit in the first blood access mode, it is possible to design the disposable with a relatively simple and straight blood flow path, thereby lowering the risk for clogging, blood leakage and hemolysis. It should be noted that, in the second blood access mode, an "essentially continuous blood flow" refers to a blood flow that is uninterrupted but may vary in flow rate, e.g. in time periods when the pumps switch between the first and second phases. These time periods are so short that the blood flow is uninterrupted. A pulsatile blood flow, on the other hand, typically comprises intermittent pulses of blood flow.

Furthermore, compared to incorporating a dedicated pneumatic or hydraulic system in a blood treatment apparatus (e.g. a dialysis machine), the inventive use of treatment fluid for operating the membrane pumps may require smaller changes to the design of the blood treatment apparatus for it to be operable with the disposable. For example, a dedicated pneumatic or hydraulic system would add significant weight and complexity to the blood treatment apparatus. To enable the inventive use of treatment fluid, the supply system is modified to generate the alternating flows of treatment fluid, at proper timing and pressure levels. As used herein, an "alternating flow of treatment fluid" refers to a flow that alternates between directed away from the supply system and being directed towards the supply system. Under the first aspect, the treatment fluid is used as a motive fluid for displacing the blood in the membrane pumps.

It is realized that the treatment fluid is a liquid substance which is manufactured and conditioned for contact with the blood, which reduces the need to test and certify the use of the treatment fluid as a motive fluid or control fluid for the membrane pump arrangement. Compared to prior art disposables that use air as motive fluid, i.e. pneumatic systems, there is little need for additional security measures to reduce any contact between the motive fluid and the blood in the membrane pumps. Leakage in pneumatic systems may result in contact between the pressurized air and the blood. This may cause air embolism. Furthermore, it may cause activation and/or coagulation of the blood, leading to increased risk of clogging, which is avoided or at least ameliorated in the disposable of the first aspect. Another technical advantage is that the treatment fluid is a liquid, which has a higher viscosity than air and thus generally leads to more silent operation of the membrane pumps. This may be an attractive feature of a blood treatment apparatus, especially if used in the home of the patient, and even more so if used for nocturnal treatment.

It is to be understood that the membrane pump arrangement may include further membrane pumps, e.g. connected in parallel with and operated in synchronization with the first and second membrane pumps. It is also conceivable that the disposable comprises membrane pump arrangements in both of the blood withdrawal and return lines.

In one embodiment, at least a subset of the upstream and downstream valves are arranged for fluid communication with the supply system and configured to be controlled by the alternating flows of treatment fluid generated by the supply system. Thus, the treatment fluid is used as control fluid for the valves. Such an embodiment, will further reduce the mechanical/electromechanical interface between the blood treatment apparatus and the disposable, since the valves do not need to be controlled by electrical signals. Furthermore, by using hydraulically controlled valves, a significant sound reduction may be achieved, e.g. compared to clamps attached on the outside of the blood lines as in the prior art, or solenoid valves which all produce distinct switching sounds.

In one embodiment, each of the upstream and downstream valves are controllable to selectively block blood flow on generation of a positive pressure in the treatment fluid. This type of valve, which may be regarded as a positive-pressure-close (PPC) valve or a negative-pressure-open (NPO) valve, is an off-the-shelf product that is well-tried in the field of hydraulic systems. In the following, this embodiment is denoted a PPC embodiment. As used herein, a "positive" pressure in a control fluid supplied to a valve refers to a pressure that exceeds the pressure of the blood inside the valve. Conversely, a "negative" pressure in the control fluid refers to a pressure that is lower than the pressure of the blood inside the valve.

In one PPC embodiment, the disposable further comprises a first line arrangement connected to the working fluid compartment of the first membrane pump, to the upstream valve of the first membrane pump and to the downstream valve of the second membrane pump, and a second line arrangement connected to the working fluid compartment of the second membrane pump, to the upstream valve of the second membrane pump and to the downstream valve of the first membrane pump. In such an embodiment, the first and second line arrangements are configured for connection to the supply system, which via the alternating flows is operable to generate alternating positive and negative pressure in the treatment fluid in the first line arrangement while simultaneously generating alternating negative and positive pressure in the treatment fluid in the second line arrangement.

In one PPC embodiment, the disposable further comprises a first and a second control valve arranged at the upstream end and the downstream end, respectively, and operable between a branched state, in which blood flow is directed through the first and second blood line branches, and a non-branched state in which blood flow is directed only through the second blood line branch. In such an embodiment, the disposable may be configurable for operation in the first blood access mode by setting the first and second control valves in the non-branched state, and in the second blood access mode by setting the first and second control valves in the branched state.

This embodiment enables a simple switching between the first and second blood access modes, by setting first and second control valves either manually, or electronically by the blood treatment apparatus. It is also possible to design the first and second control valves to visually indicate to the user that the disposable is set in a particular blood access mode. Furthermore, the embodiment may enable the disposable to be operated with the same flows of treatment fluid to the membrane pumps in both blood access modes. In one implementation example, the first and second control valves are three-way valves with one input port and two output ports connected to the first and second blood line branches, where the one of the output ports is closed in the non-branched state, while both output ports are open in the branched state. In another implementation example, the first and second control valves are on/off valves which are arranged in the first blood line branch, near the upstream and downstream ends, and operable to switch between closing and opening the first blood line branch.

In one PPC embodiment, the first and second control valves, when set in the non-branched state, are configured to vent the blood compartment of the first membrane pump via the first blood line branch, so as to admit an exchange of treatment fluid between the working fluid compartments of the first and second membrane pumps when the disposable is operated in the first blood access mode. This may enable a simplification of the supply system for the treatment fluid, since the working fluid compartment of the first membrane pump may be used for intermediate storage of the treatment fluid when the supply system generates a negative pressure in the treatment fluid in the second line arrangement. Thereby, the supply system does not need to include a dedicated reservoir for the intermediate storage.

In an alternative PPC embodiment, the first line arrangement further comprises a third control valve for blocking and admitting treatment fluid flow between the supply system and the working fluid compartment of the first membrane pump in the first and second blood access mode, respectively. Thus, no motive fluid is supplied to the first membrane pump in the first blood access mode, such that the first membrane pump is completely deactivated in the first blood access mode.

As an alternative to the above PPC embodiments, each of the downstream valves may be controllable to selectively open for blood flow by application of the positive pressure in the treatment fluid, and each of the upstream valves may be controllable to selectively block blood flow by application of the positive pressure in the treatment fluid. In such embodiments, the above-mentioned PPC (or NPO) valves are combined with valves that may be regarded as a positive-pressure-open (PPO) valve or a negative-pressure-close (NPC) valve. In the following, these embodiments are denoted PPO-PPC embodiments.

The PPO-PPC embodiments enable a disposable that has simple blood flow paths while it allows both membrane pumps to be operated for pumping blood in not only the second blood access mode, but also in the first blood access mode. Another technical effect is that the switching between the first and second blood access modes may be achieved exclusively by controlling the supply system. Thus, the switching may be achieved without the need to manipulate dedicated valves in the blood lines, which may lead to a more robust disposable and a reduced risk of hemolysis and blood leakage. The disposable may also be designed to have blood paths without dead ends, leading to a reduced risk of clogging in the blood lines. Furthermore, compared to embodiments using check valves (see below), all of the upstream and downstream valves are actively controlled by the treatment fluid, which may result in a more reliable operation of the upstream and downstream valves and a lower pressure load on the blood in the disposable. Compared to a check valve, an actively controlled valve may also be designed with larger dimensions of its internal flow passage, leading to lower shear forces being exerted on the blood and a lower risk of hemolysis.

In one PPO-PPC embodiment, the disposable further comprises a first line arrangement connected to the working fluid compartment, the upstream valve and the downstream valve of the first membrane pump, and a second line arrangement connected to the working fluid compartment, the upstream valve and the downstream valve of the second membrane pump, wherein the first and second line arrangements are configured for connection to the supply system.

In an alternative to the PPC and PPO-PPC embodiments, all upstream and downstream valves are one-way valves. A one-way valve is a valve that allows a fluid to flow through it in only one direction, where a minimum pressure differential (known as "cracking pressure") needs to be applied over the valve for it to open. One-way valves are also known as check valves, clack valves and non-return valves. Such embodiments of the first aspect, denoted CV embodiments in the following, minimize the electromechanical interface between the blood treatment apparatus and the disposable since the all upstream and downstream valves are self-regulated. Generally, the CV embodiments share the technical advantages of the PPO-PPC embodiments, save for the above-mentioned advantages attained by actively controlling the upstream and downstream valves.

In one CV embodiment, the disposable further comprises a first line arrangement connected to the working fluid compartment of the first membrane pump, and a second line arrangement connected to the working fluid compartment of the second membrane pump, wherein the first and second line arrangements are configured for connection to the supply system.

In the PPO-PPC and CV embodiments, the disposable may be configurable for operation in the first blood access mode by the supply system via the alternating flows generating alternating positive and negative pressure in the treatment fluid in the first line arrangement while simultaneously generating alternating positive and negative pressure in the treatment fluid in the second line arrangement.

Likewise, in the PPO-PPC and CV embodiments, the disposable may be configurable for operation in the second blood access mode by the supply system via the alternating flows generating alternating positive and negative pressure in the treatment fluid in the first line arrangement while simultaneously generating alternating negative and positive pressure in the treatment fluid in the second line arrangement.

A second aspect of the invention is an apparatus for blood treatment, comprising a disposable according to the first aspect, in its various embodiments, and a supply system of treatment fluid connected to the membrane pump arrangement. The apparatus shares technical advantages with the disposable of the first aspect.

In one embodiment of the second aspect, the supply system comprises a first fluid system for pumping the treatment fluid through the blood treatment unit during said blood treatment, and a second fluid system for supplying the alternating flows of treatment fluid to the membrane pump arrangement, wherein the first and second fluid systems are operated separately during said blood treatment. By operatively separating the first and second fluid systems, each system may be separately optimized for its respective purpose, enabling a simpler design and more reliable operation of each fluid system. For example, each of the first and second fluid systems may be configured to form, when connected to the disposable, a closed fluid circuit that has one or more pumping devices for pumping the treatment fluid to and from the disposable.

In one embodiment, the supply system comprises at least one priming valve which is operable to admit treatment fluid into the first and second fluid systems for filling all fluid lines in the first and second fluid systems with treatment fluid. This embodiment allows to supply system to operate with a single source of treatment fluid.

A third aspect of the invention is a method of preparing a blood treatment apparatus for operation in one of a first blood access mode and a second blood access mode, said apparatus comprising a supply system of treatment fluid and any one of the above-mentioned PPO-PPC or CV embodiments of the disposable according to the first aspect. The method of the third aspect comprises: preparing the blood treatment apparatus for operation in the first blood access mode by configuring the supply system to generate alternating positive and negative pressure in the treatment fluid in the first line arrangement while simultaneously generating alternating positive and negative pressure in the treatment fluid in the second line arrangement; and preparing the blood treatment apparatus for operation in the second blood access mode by configuring the supply system to generate alternating positive and negative pressure in the treatment fluid in the first line arrangement while simultaneously generating alternating negative and positive pressure in the treatment fluid in the second line arrangement. The method shares technical advantages with the PPO-PPC and CV embodiments of the first aspect.

A fourth aspect of the invention is a method of preparing a blood treatment apparatus for operation in one of a first blood access mode and a second blood access mode, said apparatus comprising a supply system of treatment fluid. The method comprises: obtaining a disposable comprising: a blood treatment unit; a blood withdrawal connector which is connected to the blood treatment unit via a blood withdrawal line; a blood return connector which is connected to the blood treatment unit via a blood return line; wherein one of the blood withdrawal line and the blood return line comprises a membrane pump arrangement operable to pump blood through the blood treatment unit; wherein the membrane pump arrangement comprises first and second blood line branches that are connected at an upstream end and at a downstream end, wherein a first membrane pump is arranged in the first blood line branch, and a second membrane pump is arranged in the second blood line branch; connecting the blood treatment unit to the supply system for generating a flow of treatment fluid through the blood treatment unit; if the apparatus is to be prepared for operation in the first blood access mode in which the blood withdrawal and blood return connectors are connected to a single access device, manipulating the disposable to block blood flow to and from the first membrane pump, and configuring the second membrane pump to alternately draw blood from the upstream end and pump blood through the downstream end, so as to generate a pulsatile flow of blood through the blood treatment unit; and if the apparatus is to be prepared for operation in the second blood access mode in which the blood withdrawal and blood return connectors are connected to a first and a second access device, respectively, configuring the first and second membrane pumps to concurrently draw blood from the upstream end and pump blood through the downstream end, so as to generate an essentially continuous flow of blood through the blood treatment unit.

By allowing the disposable to be operated to generate a pulsatile flow of blood through the blood treatment unit in the first blood access mode, it is possible to operate the disposable with a relatively simple and straight blood flow path in both modes. It is also possible to achieve the switching into the first blood access mode by simply blocking the blood flow through the first membrane pump. Thus, the method of the fourth aspect does not require the blood treatment apparatus to change the commutation of the first and second membrane pumps in order to switch between the modes, although it is possible that the method involves a step of disabling the first membrane pump, if the apparatus is to be operated in the first blood access mode.

The blood path may be blocked in a multitude of different ways. For example, the disposable may comprise a first and a second control valve arranged at the upstream end and the downstream end, respectively, and operable between a branched state, in which blood flow is directed through the first and second blood line branches, and a non-branched state in which blood flow is directed only through the second blood line branch. The disposable may be configurable for operation in the first blood access mode by (manually or electronically) setting the first and second control valves in the non-branched state, and in the second blood access mode by (manually or electronically) setting the first and second control valves in the branched state. For implementation examples, reference is made to the discussion further above. In a rudimentary implementation, the blood path is blocked by manually clamping the first blood line branch on both sides of the first membrane pump.

The method may implemented to use a PPC embodiment of the disposable, in which each of the first and second membrane pumps comprises a pumping chamber and a flexible member separating the pumping chamber into a blood compartment and a working fluid compartment and being movable within the pumping chamber so as to vary the volume relationship between the blood compartment and the working fluid compartment, wherein the blood compartment is arranged for fluid communication with the upstream and downstream ends, and the working fluid compartment is arranged for fluid communication with the supply system, and wherein each of the first and second membrane pumps comprises an upstream valve and a downstream valve which are connected for fluid communication with the supply system and controllable to selectively block blood flow on generation of a positive pressure in the treatment fluid. With such use, the method may further comprise: connecting the disposable to the supply system for generating alternating flows of treatment fluid to the working fluid compartments of the first and second membrane pumps, and to the upstream and downstream valves, so as to cause the first and second membrane pumps to concurrently draw blood from the upstream end and pump blood through the downstream end.

When using such a PPC embodiment, the method may further comprise, if the apparatus is to be operated in the first blood access mode, manipulating the disposable to block the flow of treatment fluid to and from the working fluid compartment of the first membrane pump. Thereby, no motive fluid is supplied to the first membrane pump which will be disabled. For example, the disposable may be configurable for operation in the first blood access mode by (manually or electronically) closing a dedicated control valve in the supply system or the disposable. In a rudimentary implementation, the flow of treatment fluid to the working fluid compartment is blocked by manually clamping a supply line for the working fluid compartment of the first membrane pump.

A fifth aspect of the invention is a disposable configured for use in one of a first blood access mode and a second blood access mode in blood treatment. The disposable comprises: a blood treatment unit for connection to a supply system operable to pump a treatment fluid through the blood treatment unit during said blood treatment; a blood withdrawal connector which is connected to the blood treatment unit via a blood withdrawal line; a blood return connector which is connected to the blood treatment unit via a blood return line; wherein one of the blood withdrawal line and the blood return line comprises a membrane pump arrangement operable to pump blood through the blood treatment unit; wherein the membrane pump arrangement comprises first and second blood line branches that are connected at an upstream end and at a downstream end, wherein a first membrane pump is arranged in the first blood line branch, and a second membrane pump is arranged in the second blood line branch; wherein each of the first and second membrane pumps comprises a pumping chamber and a flexible member separating the pumping chamber into a blood compartment and a working fluid compartment and being movable within the pumping chamber so as to vary the volume relationship between the blood compartment and the working fluid compartment, wherein the blood compartment is arranged for fluid communication with the upstream and downstream ends, and the working fluid compartment is arranged for fluid communication with the supply system; wherein each of the first and second membrane pumps comprises an upstream valve and a downstream valve which are connected for fluid communication with the supply system and controllable to selectively block blood flow on generation of a positive pressure in the treatment fluid; and wherein the disposable is configured for the first blood access mode by first-type flow directors being fixedly arranged at the upstream and downstream ends to direct the blood via only the second blood line branch, and for the second blood access mode by second-type flow directors being fixedly arranged at the upstream and downstream ends to direct the blood via the first blood line branch and the second blood line branch.

The disposable of the fifth aspect is similar to the above-mentioned PPC embodiments, and shares advantages with these embodiments. However, the disposable is configured to be used in only one of the first and second blood access modes, and is therefore provided in two versions: a first mode version and a second mode version. These versions may be identical except for the use of first-type and second-type flow directors. This allows for efficient manufacturing, since a production line may be simply modified to use either first-type and second-type flow directors to produce both versions of the disposable. Although the first-type and second-type flow directors may be different components, it is also conceivable that one and the same component may implement the first-type and second-type flow directors depending on how it is mounted in the disposable.

In one embodiment, the disposable further comprises a first line arrangement connected to the working fluid compartment of the first membrane pump, to the upstream valve of the first membrane pump and to the downstream valve of the second membrane pump, and a second line arrangement connected to the working fluid compartment of the second membrane pump, to the upstream valve of the second membrane pump and to the downstream valve of the first membrane pump, and the first and second line arrangements are configured for connection to the supply system, which is operable to generate alternating positive and negative pressure in the treatment fluid in the first line arrangement while simultaneously generating alternating negative and positive pressure in the treatment fluid in the second line arrangement. Thereby, the disposable that is equipped with the first-type flow directors is operable in the first blood access mode by connecting the blood withdrawal and blood return connectors to a single access device, and the disposable that is equipped with the second-type flow directors is operable in the second blood access mode by connecting the blood withdrawal and blood return connectors to a first and a second access device, respectively.

In one embodiment, the first-type flow directors are connected to the first blood line branch so as to vent the blood compartment of the first membrane pump via the first blood line branch. Thereby, the working fluid compartment of the first membrane pump may be used for intermediate storage of the treatment fluid when the disposable is operated in the first blood access mode.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

FIGS. 11A-11B illustrate an example of a CV embodiment operating in a first phase of a DN mode and an SN mode, respectively.

FIGS. 12A-12B are section views of an exemplary PPO valve in a closed and open state, respectively.

DETAILED DESCRIPTION OF EXAMPLE EMBODIMENTS

Figure 1:
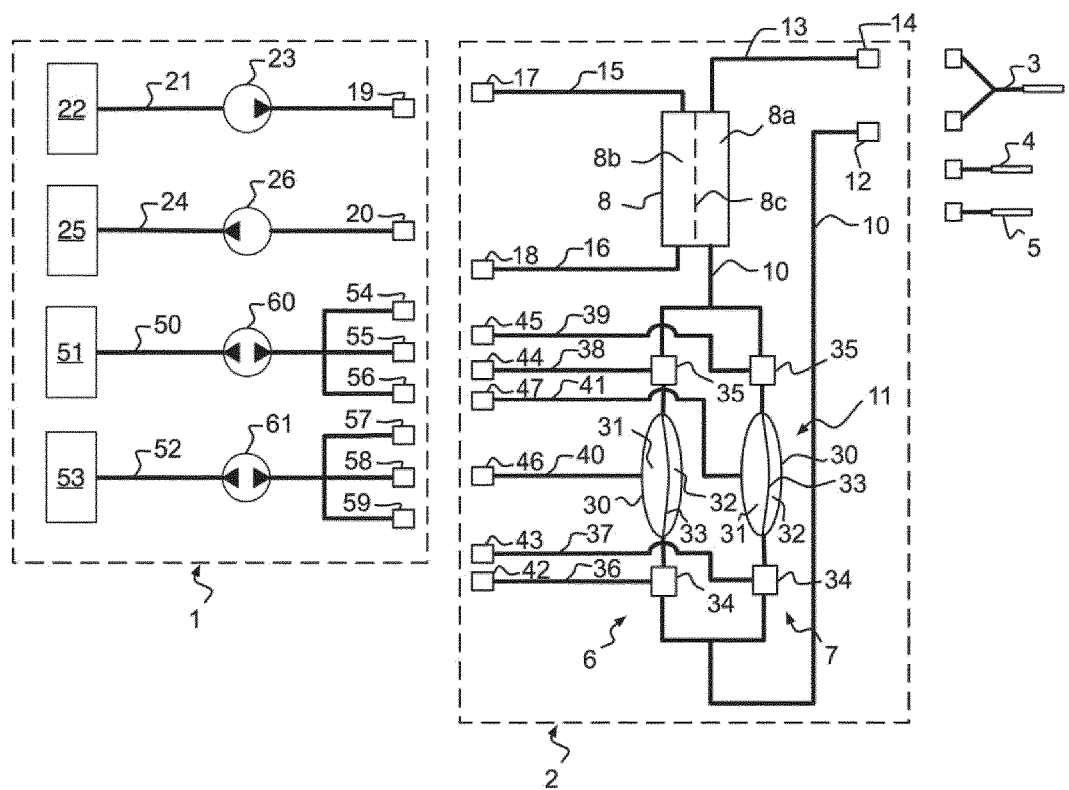
FIG. 1 illustrates a diagram of a disposable together with a supply system and a set of access devices.

The following description is intended to illustrate a few embodiments of a disposable for use in a blood treatment apparatus, in particular a dialysis machine for blood treatment therapy. Furthermore, a few examples are given on systems for supplying treatment fluid to the disposable, as well as different types of valves that may be suitable for use in the disposable.

Throughout the description, the same reference numerals are used to identify corresponding elements.

FIG. 1 illustrates a combination of a supply system 1 for treatment fluid, a disposable 2 and a set of access devices 3-5. The supply system 1 is part of a machine unit, also known as a "monitor" (not shown), and is configured for preparing, conditioning and supplying treatment fluid (dialysis fluid) to the disposable 2. A dialysis machine is formed by functionally connecting the disposable 2 to the machine unit and to one or more of the access devices 3-5. In addition to the supply system 1, the machine unit may include an electronic interface, control electronics, a graphical user interface, etc. The control electronics may be at least partly operated under control of software instructions executed by a processor in the machine unit. The control electronics may e.g. control the operation of the dialysis machine, including the operation of pumping devices in the supply system 1, and the opening and closing of various flow controllers such as valves, clamping devices in the supply system 1 and, possibly, in the disposable 2. The control electronics may also generate feedback or instructions to the operator of the machine. Further, the control electronics may acquire and process signals from various sensors in the supply system 1 and the disposable 2, e.g. for use in controlling the operation of the dialysis machine as well as for executing safety functions implemented to identify or prevent potential fault conditions. The skilled person thus realizes that the structure illustrated in FIG. 1 may be supplemented by other components, not further described herein.

The disposable 2 is a unitary device which may be formed as an aggregation of discrete components or as an integrated unit. The integrated unit may be implemented as a cassette, cartridge, support structure, etc to be installed in a dedicated mounting area on the machine unit. Preferably, the disposable 2 is designed to interface with the machine unit in a "one-click" action, which thus results in a complete functional connection between the disposable 2 and the supply system 1, as will be described in the following.

In the illustrated embodiment, the disposable 2 contains two membrane pumps 6, 7 for blood transport, where the dialysis fluid is used as a medium (motive fluid) to energize the blood transport. The dialysis fluid is also used for controlling the blood flow via the commutation of the membrane pumps 6, 7.

The disposable 2 comprises a blood treatment unit 8, which may be any type of blood filter device, such as a coil dialyzer, a parallel plate dialyzer, a hollow fiber dialyzer, etc. For simplicity, the blood treatment unit 8 is denoted "dialyzer" in the following. The dialyzer 8 has a blood side 8a and a dialysis fluid side 8b separated by a semipermeable membrane 8c. An inlet on the blood side 8a is connected to a blood withdrawal line 10, which includes a pump arrangement 11 and extends to a connector 12. An outlet on the blood side 8a is connected to a blood return line 13 which extends to a connector 14. The connectors 12, 14 form a mechanical interface for connecting the disposable 2 to connectors of the access device(s) 3-5. The access devices 3-5 may be of any suitable type, such as a cannula, a needle, a catheter, etc, and may be arranged for connection to any suitable vascular access, such as fistula, a graft, a Scribner-shunt, a peripheral vein, etc, on any part of the body of the patient to be treated.

The dialysis fluid side 8b of the dialyzer 8 has an inlet and an outlet which are connected to an inlet line 15 and an outlet line 16, respectively, which extend to a respective connector 17, 18. The connectors 17, 18 form a mechanical interface for connecting the dialyzer 8 to connectors 19, 20 in the supply system 1. The supply system 1 includes a first supply line 21 which extends from a reservoir 22 to the connector 19 and includes a first fluid pump 23, and a second supply line 24 which extends from the connector 20 to a sink 25 and includes a second fluid pump 26. When the supply system 1 is functionally connected to the dialyzer 8, the pumps 23, 26 are controlled to generate a flow of dialysis fluid from the reservoir 22, through the dialysis fluid side 8b of the dialyzer 8 to the sink 25 which receives spent dialysis fluid. The sink 25 may be a dedicated container or a drain. The pumps 23, 26 may be of any suitable type for pumping dialysis fluid through a tubing, e.g. a roller or peristaltic pump, a gear pump, a centrifugal pump, etc.

The pump arrangement 11 in the disposable 2 is formed by two membrane pumps 6, 7 that are connected in parallel in the withdrawal line 10. As shown, a first membrane pump 6 is arranged in a first line branch and a second membrane pump 7 is arranged in a second line branch. The line branches are connected at upstream and downstream ends (branch points). As used herein, "upstream" and "downstream" refers to positions further up and down, respectively, from the pump arrangement 11 in relation to the flow of blood. Thus, when the disposable 1 is functionally connected to the access device(s), the first and second pumps 6, 7 are controlled to generate a flow of blood from the upstream end and push blood towards the downstream end.

Each of the membrane pumps 6, 7 has a pumping chamber 30, which is separated into first and second accumulation compartments 31, 32 by a flexible member 33, e.g. in the form of a soft/elastic membrane. The flexible member 33 is movable within the pumping chamber 30 so as to vary a volume relationship between the first and second accumulation compartments 31, 32. Further, the first accumulation compartment 31 (working fluid compartment) is configured to receive an amount of dialysis fluid from the supply system 1, and the second accumulation container 32 (blood compartment) is configured to receive an amount of untreated blood from the patient. Hence, in the illustrated embodiment, the dialysis fluid may act on the blood with the flexible member 33 as a separating interface. Consequently, the dialysis fluid is used for energizing the blood transport.

In one embodiment, the membrane 33 is molded from a soft polymeric material and designed not to be stretched during operation. In one embodiment, the membrane 33 is preformed into a dome shape that matches the shape of the inner surface of the pumping chamber 30. A gasket for sealing may be integrated in the periphery of the membrane 33. In order to ensure that the outlet of the blood compartment 32 is not closed by the membrane 33 before the blood compartment 32 is sufficiently emptied of blood, the membrane 33 may have an increasing thickness towards its periphery, so that the thickest portion is at the outlet. Furthermore, the inner surfaces of the working fluid compartment 31 and the blood compartment 32 may be equipped with grooves, extending from inlet to outlet, to facilitate filling and emptying of the compartments 31, 32.

To allow the disposable 2 to operate in a desired manner, each of the membrane pumps 6, 7 includes first and second blood valves 34, 35. The first blood valve 34 is configured to control the extraction of untreated blood from the patient via the access device attached to connector 12, and the second blood valve 35 is configured to control the transport of blood through the dialyzer 8 and back to the patient via the access device attached to connector 14. By activating the blood valves 34, 35 alternately, such that the first blood valve 34 is open while the second blood valve 35 is closed, and vice versa, each membrane pump 6, 7 is controlled to alternate between an intake phase and an outlet phase. In the intake phase, blood enters the pumping chamber 30 from the upstream end and in the outlet phase blood is expelled from the pumping chamber 30 towards the downstream end. The switching between intake and outlet phases is commonly referred to as "commutation". Hence, the blood valves 34, 35 may be referred to as "commutation valves". In the illustrated embodiment, the blood valves 34, 35 are configured to be hydraulically controlled, and specifically by the pressure of the dialysis fluid supplied to a control side of the valves 34, 35.

As shown, supply lines 36-41 extend from the valves 34, 35 and the working fluid compartments 31 of the membrane pumps 6, 7 to a respective connector 42-47. The connectors 42-47 form a mechanical interface for connecting the pump arrangement 11 to the supply system 1. The supply system 1 includes a first control line 50 which extends from a first control reservoir 51 to a first set of connectors 54-56, and a second control line 52 which extends from a second control reservoir 53 to a second set of connectors 57-59. Each of the first and second control lines 50, 52 includes a control pump 60, 61 which is operable to pump the dialysis fluid both directions in the respective control line 50, 52. When the supply system 1 is functionally connected to the disposable 2, the control pumps 60, 61 are controlled to generate alternating flows of dialysis fluid from the control reservoirs 51, 53 to the pump arrangement 11, so as to generate alternating pressures in the working fluid compartments 31 and at the valves 34, 35.

It is to be understood that the number of connectors in the mechanical interface between the supply system 1 and the pump arrangement 11 may be reduced. For example, the supply lines 36-41 may be arranged in groups of three, each with a common connector for attachment to a single connector in the first and second control lines 50, 52, respectively.

As will be exemplified in more detail below, the disposable 2 may be set to operate in either of a double-needle (DN) mode and in a single-needle (SN) mode.

In DN mode, the connectors 12, 14 are attached to access devices 4, 5, and the membrane pumps 6, 7 are controlled to operate with opposite intake and outlet phases. Looking at the pump arrangement 11 as a unit, it will operate to alternate between a first phase (DN-P1) and a second phase (DN-P2). In DN-P1, blood is expelled from the blood compartment 32 of the first pump 6 and drawn into the blood compartment 32 of the second pump 7. In DN-P2, blood is drawn into the blood compartment 32 of the first pump 6 and expelled from the blood compartment 32 of the second pump 7. Thus, in DN mode, the pump arrangement 11 generates an essentially continuous flow of blood into the withdrawal line 10, through the dialyzer 8 and out of the return line 13.

In SN mode, the connectors 12, 14 are attached to access device 3, and the pump arrangement 11 is controlled to alternate between a first phase (SN-P1) and a second phase (SN-P2). In SN-P1, blood is drawn into the pump arrangement 11, and in SN-P2 blood is expelled from the pump arrangement 11, which thereby generates a pulsatile flow of blood through the dialyzer 8. There are various ways of achieving the first and second phases in SN mode, depending on the characteristics of the blood valves 34, 35, as will be explained below.

FIGS. 2-3 illustrate a pump arrangement 11 in which all blood valves 34, 35 are designed to close on application of a positive pressure (of a predetermined magnitude) on the control side, and to otherwise be open. This type of valve is denoted a Positive Pressure Closed (PPC) valve. As used herein, a blood valve is "closed" when it blocks the flow of blood, and "open" when it allows a through-flow of blood. In the illustrated embodiment, the upstream blood valve 34 and the working fluid compartment 31 of pump 6 and the downstream blood valve 35 of pump 7 are all connected to the first control line 50, whereas the downstream valve 35 of pump 6 and the upstream blood valve 34 and the working fluid compartment 31 of pump 7 are all connected to the second control line 52.

Figures 2A, 2B:
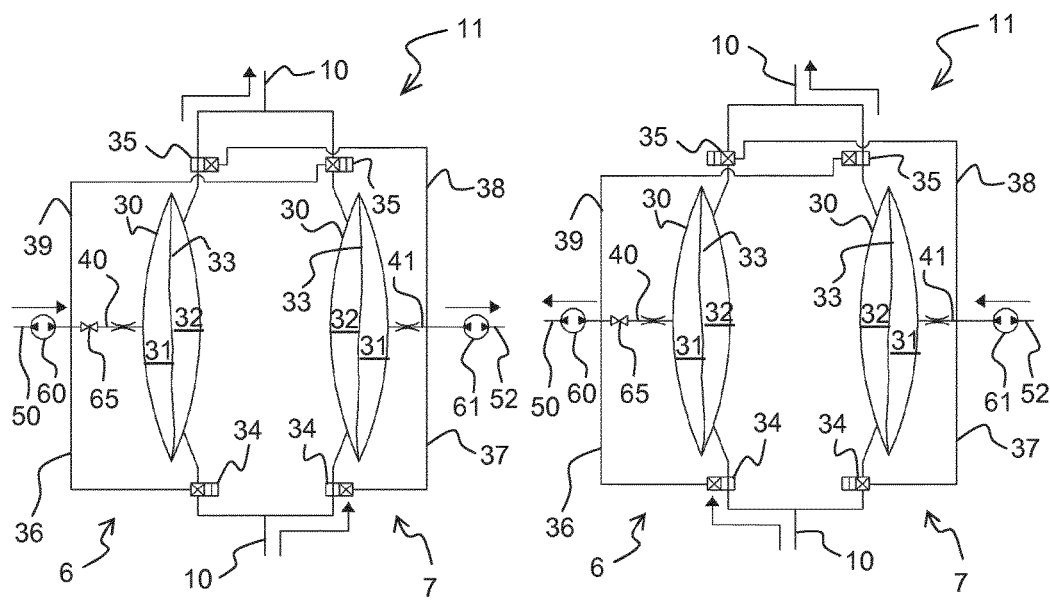
FIGS. 2A-2B illustrate a first example of a PPC embodiment operating in a first phase and a second phase, respectively, of a DN mode.

FIGS. 2A-2B illustrate the first and second phases (DN-P1, DN-P2) of the pump arrangement 11 when the disposable 2 is operated in DN mode. The flows of dialysis fluid and blood are indicated by thick arrows. To set the disposable 2 in DN mode, the control pumps 60, 61 in the supply system 1 are controlled to generate mutually opposite flows of dialysis fluid in the first and second control lines 50, 52. In FIG. 2A, DN-P1 is generated by concurrently pumping dialysis fluid into the pump arrangement 11 via control line 50 and out of the pump arrangement 11 via control line 52. In FIG. 2B, DN-P2 is generated by concurrently pumping dialysis fluid into the pump arrangement 11 via control line 52 and out of the pump arrangement 11 via control line 50.

Figures 3A, 3B:
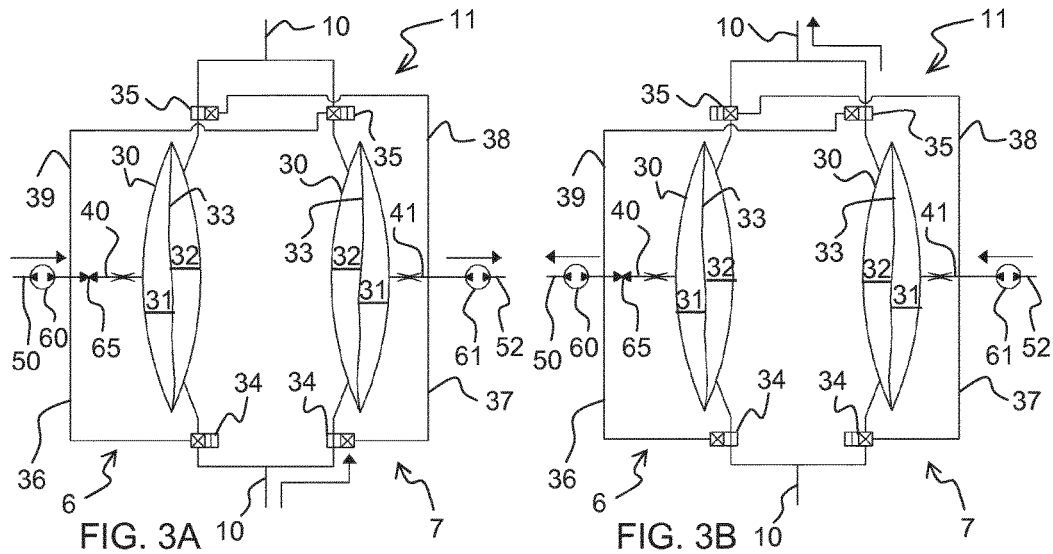
FIGS. 3A-3B illustrate the first example operating in a first phase and a second phase, respectively, of an SN mode.

FIGS. 3A-3B illustrate the first and second phases (SN-P1, SN-P2) of the pump arrangement 11 when the disposable 2 is operated in SN mode. To set the disposable 2 in SN mode, a two-way on/off valve 65 is operated to close the supply line 40 to the working fluid compartment 31 of pump 6, while the control pumps 60, 61 are controlled to generate mutually opposite flows of dialysis fluid in the first and second control lines 50, 52. The on/off valve 65 may be of any type, including but not limited to a pinch valve, a ball valve, a gate valve, knife valve and a plug valve. In the embodiment of FIGS. 2-3, the on/off valve 65 is part of the disposable 2, where the on/off valve 65 may be manually closed and opened by the operator, or electronically operated, e.g. by the above-mentioned control electronics. In a further variant (not shown), the on/off valve 65 is included in the supply system 1 and operable to prevent flow of dialysis fluid to and from the working fluid compartment 31 of pump 6. In yet another alternative, the on/off valve 65 is a separate component which is manually attached to the disposable 2 when the disposable 2 is to be operated in SN mode. In FIG. 3A, SN-P1 is generated by concurrently pumping dialysis fluid into the pump arrangement 11 via control line 50 and out of the pump arrangement 11 via control line 52. In FIG. 3B, SN-P2 is generated by concurrently pumping dialysis fluid into the pump arrangement 11 via control line 52 and out of the pump arrangement 11 via control line 50.

Figures 4A, 4B:
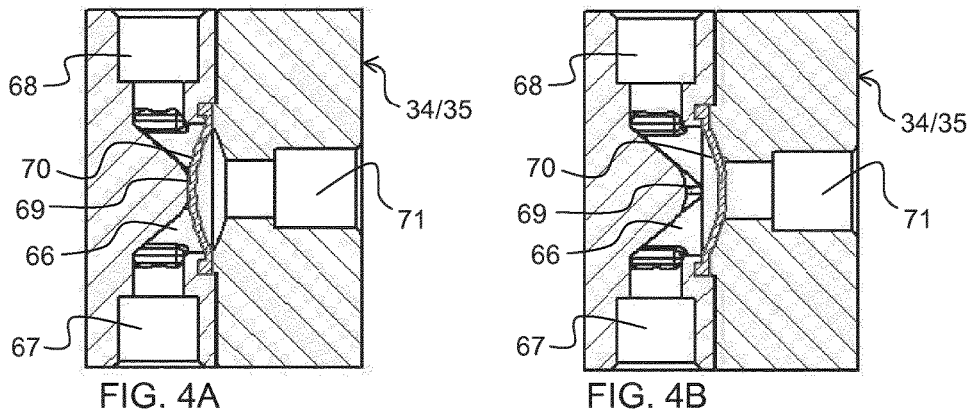
FIGS. 4A-4B are section views of an exemplary PPC valve in a closed and open state, respectively.

The hydraulically controlled PPC valve is a standard component. A non-limiting example of a PPC valve is illustrated in FIGS. 4A-4B. The valve defines an internal blood flow passage 66 between an inlet 67 and an outlet 68. A protrusion 69 in the blood flow passage 66 forms a valve seat for a resilient or flexible membrane 70, which is arranged to cover an opening between a control fluid channel 71 and the blood flow passage 66. When a sufficient positive hydraulic pressure is applied in the control fluid channel 71, as shown in FIG. 4A, the membrane 70 is deformed into engagement with the protrusion 69, thereby blocking the blood flow passage 66. Depending on the configuration of the membrane 70, the blocking action may be released by relaxation of the positive pressure or by active application of a negative pressure in the control fluid channel 71 (FIG. 4B).

Figures 5A, 5B:
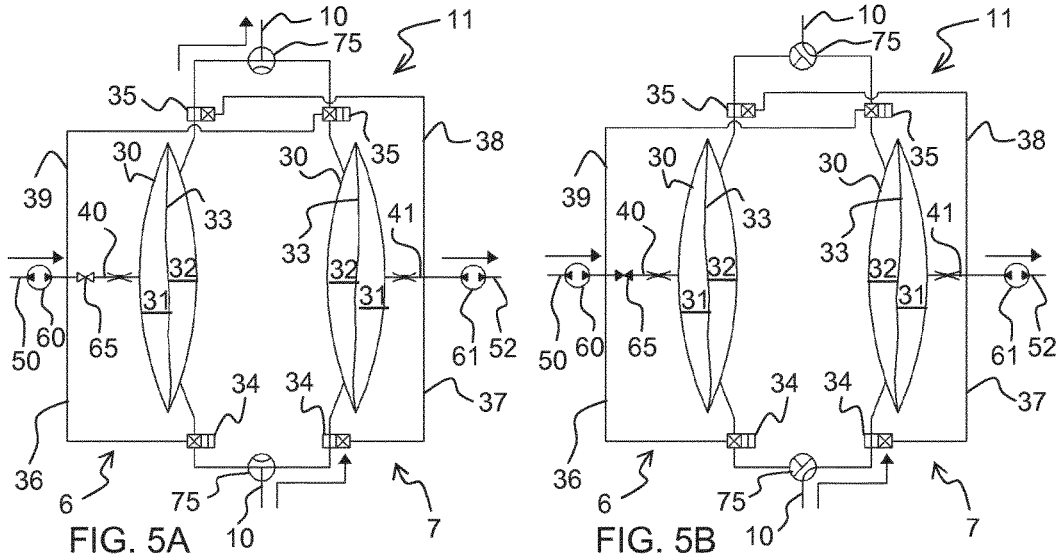
FIGS. 5A-5B illustrate a second example of a PPC embodiment operating in a first phase of a DN mode and an SN mode, respectively.

Reverting to FIG. 3, it may be noted that the withdrawal line 10 will have "dead ends" in SN mode, between the branch points and the blood valves 34, 35. FIG. 5 illustrates a pump arrangement 11 with PPC valves 34, 35 that eliminates or at least minimizes the presence of dead ends in the blood flow path in SN mode. This is achieved by the use of flow directors 75 which are mounted to define the branching points. Each flow director 75 may be implemented as a three-way valve which may be switched between a first position, in which fluid communication is established between an inlet and two outlets (a branched position), and a second position, in which fluid communication is established between the inlet and only one of the outlets (non-branched position). The three-way valve 75 may e.g. be rotated between the first and second positions. FIG. 5A illustrates the pump arrangement 11 set in DN mode (and operating in phase DN-P1), by the flow directors 75 being set in the branched position. FIG. 5B illustrates the pump arrangement 11 set in SN mode (and operating in phase SN-P1), by the flow directors 75 being set in the non-branched position.

As an alternative to the embodiment of FIG. 5, it is conceivable to use the pump arrangement 11 in FIG. 3 and set it into SN mode by manually applying clamps to the first or second branch line, e.g. adjacent to each of the two branch points, so as to block the blood flow through one of the branch lines, i.e. to and from one of the membrane pumps 6, 7.

Figure 6:
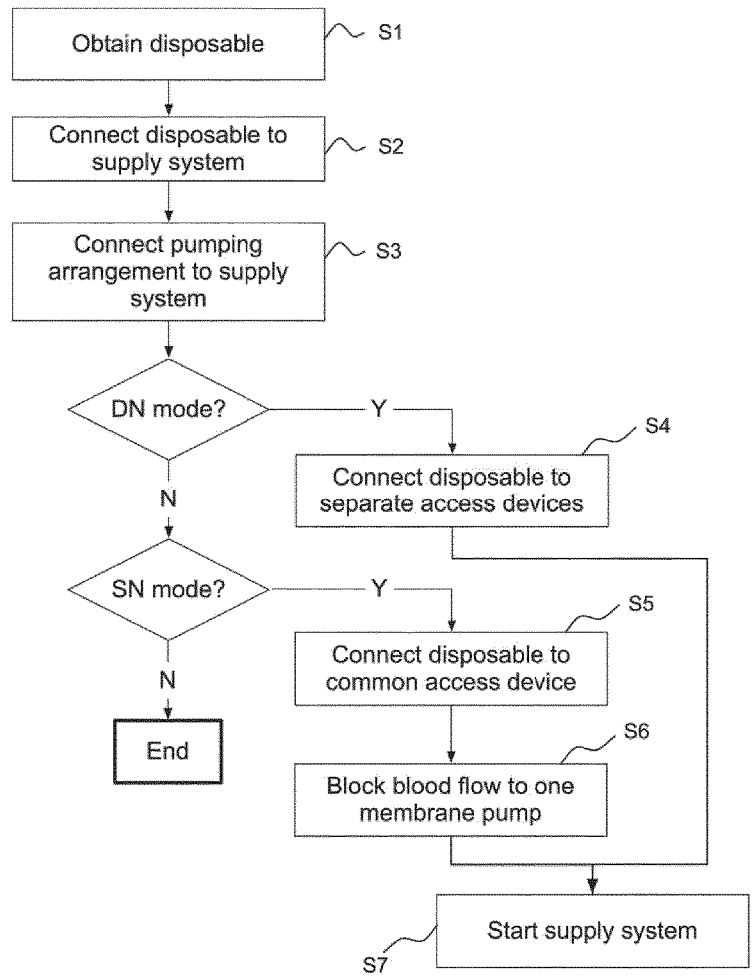
FIG. 6 is a flow chart of a method for operating a PPC embodiment in either DN mode or SN mode.

The use of flow directors 75, or manual clamps, may be seen as a method of preparing a blood treatment apparatus for operation in either a DN mode and an SN mode, as illustrated in the flow chart of FIG. 6. In step S1, the operator obtains a disposable 2 with parallel membrane pumps 6, 7, PPC valves 34, 35 and a dialyzer 8 as disclosed herein. In step S2, the disposable 2 is connected to a supply system 1 for generating a flow of dialysis fluid through the dialyzer 8. In step S3, the membrane pumps 6, 7 are connected to the supply system 1 for generating the required alternating flows of dialysis fluid. If the blood treatment apparatus is to be operated in DN mode, the connectors 12, 14 are connected to separate access devices 4, 5 (step S4). If the blood treatment apparatus is to be operated in SN mode, the connectors 12, 14 are connected to a common access device 3 (step S5) and the disposable 2 is manipulated (step S6) to block blood flow to and from one of the membrane pumps 6, 7, e.g. by manually or electronically turning the flow controller 75 or by manually applying clamps. Step S6 may also comprise disabling the membrane pump 6 by manually or electronically closing the on/off valve 65. In step S7, the supply system 1 is started to operate the disposable 2 in the selected mode. It should be noted that the method of blocking the blood flow to and from one of the membrane pumps 6, 7 is also applicable when the blood valves 34, 35 and/or the pumping chambers 30 are controlled by other means than by flows of dialysis fluid, e.g. by electrical signals or pneumatic pressure, or by hydraulic pressure in a liquid other than dialysis fluid.

Reverting to FIG. 5, it is also conceivable to use two different types of flow directors 75 which, at manufacture of the disposable 2, are fixedly arranged to define the branch points. This will result in two product versions of the disposable 2: a DN version with one type of flow director 75, and an SN version with another type of flow director 75. Thus, FIG. 5A may be seen to illustrate such a DN version, and FIG. 5B may be seen to illustrate an SN version. Both product versions are based on the same components, except for the flow directors 75, and may be manufactured in an efficient way. In fact, it is possible to use the same flow director 75 for both product versions, e.g. if the flow director 75 is designed to be mounted in two different rotations resulting in the branched state (FIG. 5A) and the non-branched state (FIG. 5B).

Figures 7A, 7B:
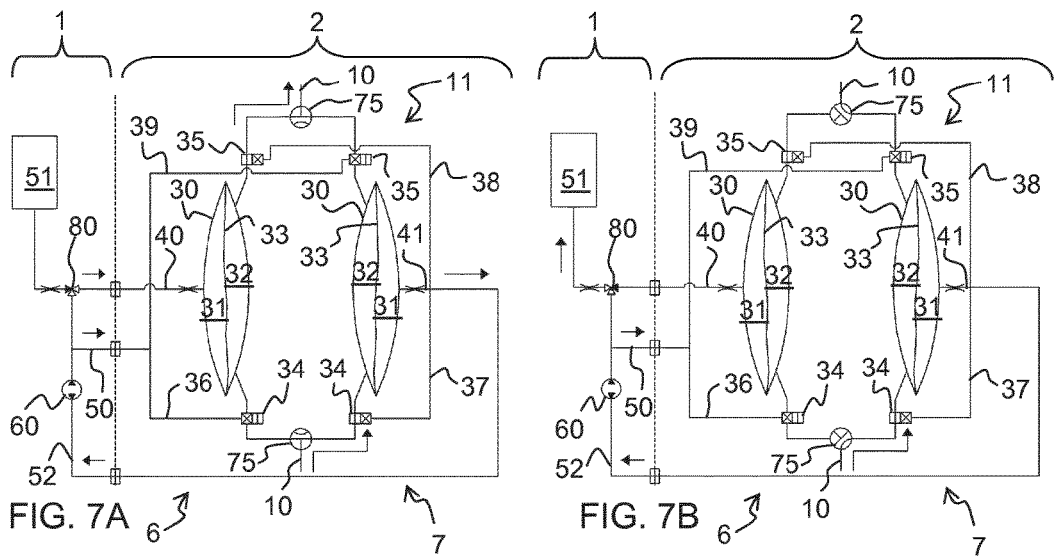
FIGS. 7A-7B illustrate a third example of a PPC embodiment operating in a first phase of a DN mode and an SN mode, respectively.

All embodiments presented so far have a supply system 1 with two control pumps 60, 61 for generating the opposite flows of dialysis fluid to the pump arrangement 11. It should be understood that other designs are possible. FIG. 7 illustrates a supply system 1 (left of the dashed line) with only one control pump 60 and one reservoir 51, wherein a control valve 80 is arranged to selectively close and open a flow path between the control pump 60 and the reservoir 51. In the example of FIG. 7, the control valve 80 is implemented as a three-way valve which also embodies the function of the on/off valve 65 in FIG. 5, which thereby is part of the supply system 1 instead of the disposable 2. In FIG. 7A, the disposable 2 is operated in DN mode (phase DN-P1), by the control valve 80 closing the flow path between the pump 60 and the reservoir 51, and opening the flow path between the pump 60 and the working fluid compartment 31 of pump 6. In FIG. 7B, the disposable 2 is operated in SN mode (phase SN-P1), by the control valve 80 opening the flow path between the pump 60 and the reservoir 51, and closing the flow path between the pump 60 and the working fluid compartment 31 of pump 6. It should be realized that this supply system 1 may also be used in combination with the disposable in FIGS. 2-3, but with the control valve 80 implemented as a two-way on/off valve, and with the supply line 40 (containing the on/off valve 65) connected to the control line 50.

Figure 8A:
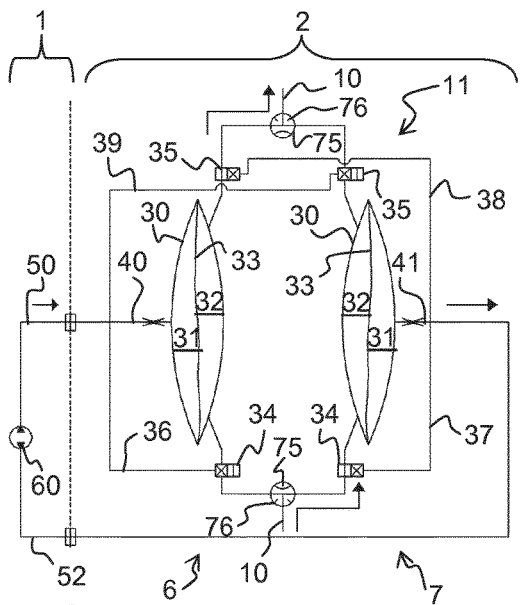
FIGS. 8A-8B illustrate a fourth example of a PPC embodiment operating in a first phase of a DN mode and an SN mode, respectively.
Figure 8B:
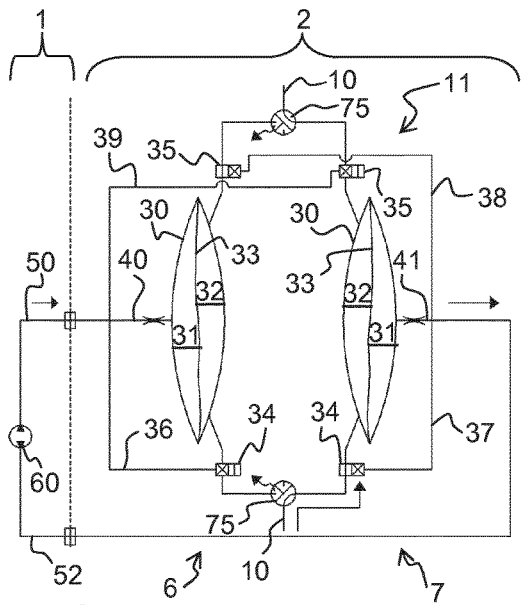

FIG. 8 illustrates a further variant of the embodiments that make use of flow directors 75. This variant enables further simplification of the supply system 1, by allowing the reservoir 51 in FIG. 7 to be omitted. Instead one of the working fluid compartments 31 is used as a reservoir when the disposable 2 is operated in SN mode. To this end, the flow directors 75 are provided with a venting channel 76, which connects the blood compartment 32 with ambient when the flow directors 75 are arranged in the second position. In FIG. 8A, the disposable 2 is operated in DN mode (phase DN-P1) in the same way as the disposable in FIG. 7A. In FIG. 8B, the flow directors 75 are turned not only to block the blood flow to and from the membrane pump 6, but also to align the venting channel 76 with the line branch of the membrane pump 6. Thereby, in SN-P1 shown in FIG. 8B, blood is drawn into the blood compartment 32 of pump 7 by the flow of dialysis fluid out of the working fluid compartment 31 created by the control pump 60, which drives the dialysis fluid into the working fluid compartment 31 of pump 6. In SN-P2 (not shown), the control pump 60 is reversed to drive the dialysis fluid from working fluid compartment 31 of pump 6 into the working fluid compartment 31 of pump 7, thereby driving blood out of blood compartment 32 of pump 7 towards the dialyzer 8 (not shown). It is realized that the same venting principle may be implemented when manufacturing different SN and DN versions of the disposable 2, as discussed in the foregoing.

Figure 9:
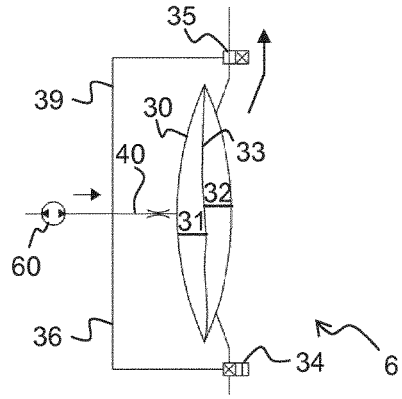
FIG. 9 illustrates a membrane pump included in a PPO-PPC embodiment.

FIG. 9 illustrates another embodiment of a membrane pump 6 for use in a disposable 2. This embodiment uses a combination of a PPC blood valve and a blood valve designed to open on application of a positive pressure (of a predetermined magnitude) on the control side, and to otherwise be close. This type of valve is denoted a Positive Pressure Open (PPO) valve. The PPC valve 34 is arranged on the upstream side and the PPO valve 35 is arranged on the downstream side of the pumping chamber 30. FIG. 9 shows the outlet phase of the membrane pump 6. This phase is controlled by the control pump 60 driving dialysis fluid into working fluid compartment 31, and to the PPC valve 34, which thereby closes, and to the PPO valve 35, which thereby opens. In the intake phase (not shown), the control pump 60 drives the dialysis fluid away from the working fluid compartment 31, and away from the PPC valve 34, which thereby opens, and away from the PPO valve 35, which thereby closes.

Figure 10A:
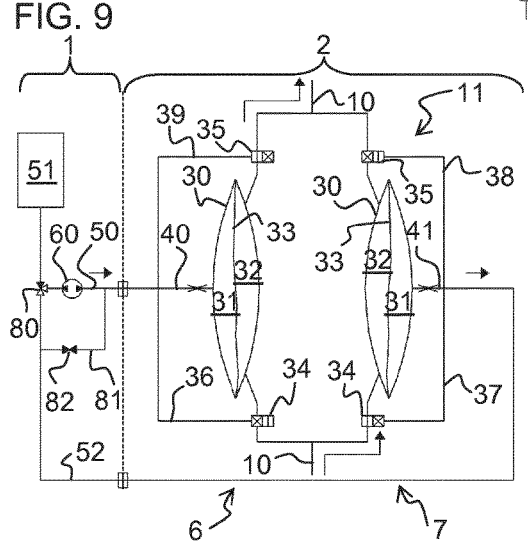
FIGS. 10A-10B illustrate an example of a PPO-PPC embodiment operating in a first phase of a DN mode and an SN mode, respectively.
Figure 10B:
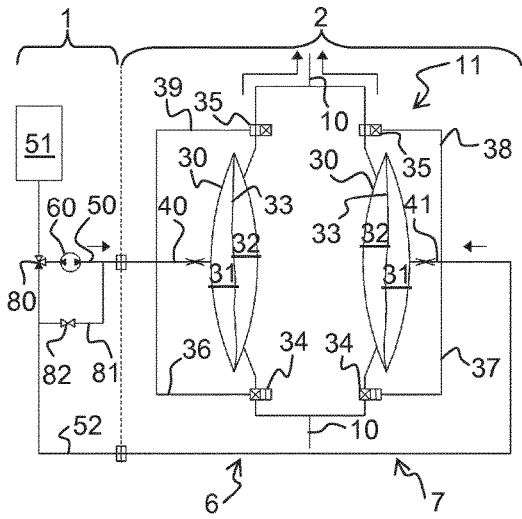

FIG. 10 illustrates a pump arrangement 11 having two membrane pumps 6, 7 of the type shown in FIG. 9. The upstream blood valves 34 are of PPC type and the downstream blood valves 35 are of PPO type. The disposable 2 is capable of being operated in DN mode and SN mode. The switching between modes is accomplished by changing the flow of dialysis fluid to and from the membrane pumps 6, 7. In DN mode, as shown in FIG. 10A, the supply system 1 is controlled to generate mutually opposite flows of dialysis fluid in the first and second control lines 50, 52, such that positive pressure is generated in one control line while a negative pressure is generated in the other control line, and vice versa. In SN mode, as shown in FIG. 10B, the supply system 1 is instead controlled to generate dialysis flows of the same direction in both control lines 50, 52, such that both control lines 50, 52 are concurrently at a positive or negative pressure. This may be achieved by use of two control pumps 60, 61 as indicated in FIG. 1. However, in the example of FIG. 10, the supply system 1 is designed to generate the required flows of dialysis fluid by way of one control pump 60, one reservoir 51, a by-pass line 81 having a two-way on/off valve 82 and extending between the first and second control lines 50, 52, and a three-way valve 80 connected to the reservoir 51, the first control line 50 and the second control line 52, respectively. By operating the three-way valve 80 to close fluid communication with the reservoir 51, while closing the on/off valve 82, mutually opposite flows of dialysis fluid are generated in the control lines 50, 52 (FIG. 10A). By instead operating the three-way valve 80 to close the fluid communication with the second control line 52, while opening the on/off valve 82 to admit a flow of dialysis fluid from the control pump 60 via the by-pass line 81 into the second control line 52, coordinated flows of dialysis fluid are generated in the control lines 50, 52 (FIG. 10B).

FIG. 11 illustrates another embodiment of a pump arrangement 11 for a disposable 2. In this embodiment, the blood valves 34, 35 are implemented as check valves which are arranged to open in the downstream direction. Like the embodiment in FIG. 10, the disposable 2 is switched between modes by changing the flow of dialysis fluid to and from the membrane pumps 6, 7. In FIG. 11A, the disposable is in DN mode (phase DN-P1) by way of opposite flows of dialysis fluid to the working fluid compartments 31. In FIG. 11B, the disposable is in SN mode (phase SN-P1) by way of coordinated flows of dialysis fluid to the working fluid compartments 31.

Returning to the embodiment of FIG. 10, it is to be understood that the hydraulically controlled PPO valve is also a standard component, albeit less common than the PPC valve.

A non-limiting example of a PPO valve is illustrated in the section views of FIGS. 12A-12B. The valve defines an internal blood flow passage 85 between an inlet 86 and an outlet 87. The blood flow passage 85 defines a conical valve seat 88 which extends to a control chamber 89. A control fluid channel 90 opens into the control chamber 89. A flow control plug 91 is arranged inside the valve and has a conical portion 92 for abutment on the valve seat 88 and a distal membrane 93 which is fixed at its periphery to seal the opening between the control chamber 89 and the control fluid channel 90. The plug 91 may be made of resilient material, such as rubber. When a sufficient positive hydraulic pressure is applied in the control fluid channel 90, as shown in FIG. 12B, the membrane 93 is deformed and the conical portion 92 slides upward, leaving a space between the plug 91 and the valve seat 88, thereby opening the blood flow passage 85. Depending on the configuration of the membrane 93, the opening action may be released by relaxation of the positive pressure or by active application of a negative pressure in the control fluid channel 90 (FIG. 12A).

Figure 13A:
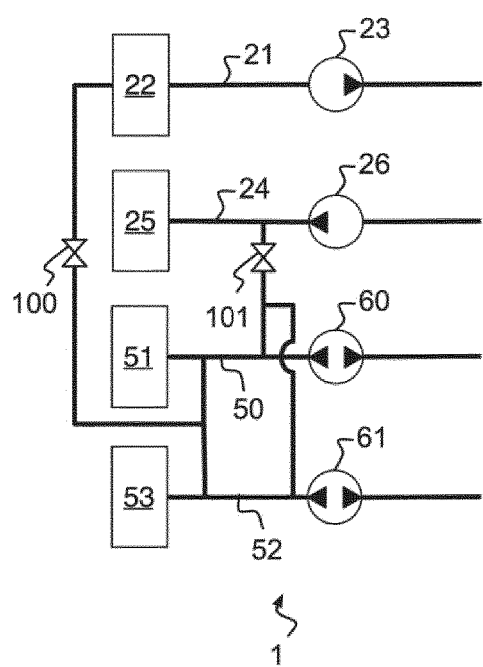
FIGS. 13A-13B illustrate alternative installations of a priming valve in supply systems of the type shown in FIG. 1 and FIG. 8, respectively.
Figure 13B:
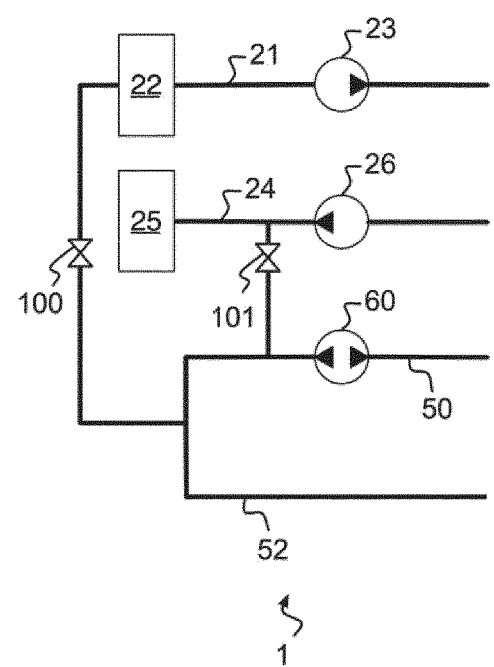

In all examples given so far, the supply system is hydraulically separated into a first fluid system for connection to the dialyzer 8 and a second fluid system for connection to the pump arrangement 11. In the example of FIG. 1, the second fluid system is in turn hydraulically separated into two sub-systems for generating separate flows of dialysis fluid to the pump arrangement 11. The separation into first and second fluid systems facilitates the design of the supply system, compared to using a single hydraulic circuit for supplying dialysis fluid to both the dialyzer 8 and the pump arrangement 11. Irrespective of implementation, it may be beneficial to connect the first and second fluid systems to a common source of dialysis fluid, via a priming valve. An example is given in FIG. 13A, which is based on the supply system 1 shown in FIG. 1, with such a priming valve 100 being arranged in a fluid line connecting the reservoir 22 of the first fluid system to the control lines 50, 52 of the second fluid system. Another example is given in FIG. 13B, which is based on the second fluid system shown in FIG. 8, with the priming valve 100 being arranged in a fluid line connecting the reservoir 22 in the first fluid system to the control line 52 of the second fluid system. In the process of connecting the first and second fluid systems to the disposable, the priming valve 100 may be opened to prime (fill) the lines of the second fluid system with dialysis fluid. In a variant, the first fluid system is connected to a source of dialysis fluid, and a priming valve is arranged between the first and second fluid systems. An example is given in FIG. 13A, where such a priming valve 101 is arranged in a fluid line connecting the supply line 24 of the first fluid system to the control lines 50, 52 of the second fluid system. Another example is given in FIG. 13B, where the priming valve 101 is arranged in a fluid line connecting the supply line 24 of the first fluid system to the control line 52 of the second fluid system. In the process of connecting the first and second fluid systems to the disposable, and subsequent to or concurrent with a priming of the first fluid system, the priming valve 101 may be opened for priming of the second fluid system.

It should emphasized, though, that the supply system may instead be configured as a single hydraulic circuit, e.g. to reduce the weight of the supply system.

It may be noted that many of the illustrated embodiments comprises a constriction (indicated by symbol ⋍) in each of the supply lines 40, 41 to the working fluid compartments 31 (see FIGS. 2, 3, 5 and 7-10). The constriction is optional, and may be implemented to increase the absolute pressure level in the dialysis fluid that acts on the blood valves 34, 35. Such a pressure increase may improve the control of the opening and/or closing of the blood valves 34, 35, e.g. to ensure safe and consistent commutation of the membrane pumps 6, 7.

While the invention has been described in connection with what is presently considered to be the most practical and preferred embodiments, it is to be understood that the invention is not limited to the disclosed embodiments, but on the contrary, is intended to cover various modifications and equivalent arrangements included within the spirit and the scope of the appended claims.

For example, the skilled person realizes that many of the above-described examples may be adapted to a disposable 2 in which only the pumping chambers 30 are connected to the supply system 1, while the blood valves 34, 35 are operated by other means, e.g. by electrical signals or pneumatic pressure, or by hydraulic pressure in a liquid other than dialysis fluid. The same applies to a disposable 2 in which the blood valves 34, 35 are connected to the supply system 1, while the pumping chambers 30 are operated by other means.

It should also be understood that the inventive concept is applicable to different types of blood treatment therapy, including but not limited to hemodialysis (HD), hemofiltration (HF), and hemodiafiltration (HDF).

The invention claimed is:

1. An apparatus for blood treatment, the apparatus comprising:
    a supply system of a treatment fluid; and
    a disposable for use in blood treatment, the disposable comprising a blood treatment unit for connection to the supply system that is operable to pump the treatment fluid through the blood treatment unit during the blood treatment, a blood withdrawal connector which is connected to the blood treatment unit via a blood withdrawal line, and a blood return connector which is connected to the blood treatment unit via a blood return line,
    wherein one of the blood withdrawal and blood return lines comprises a membrane pump arrangement operable to pump blood through the blood treatment unit, wherein the membrane pump arrangement comprises first and second blood line branches that are connected at an upstream end and at a downstream end, wherein a first membrane pump is arranged in the first blood line branch, and a second membrane pump is arranged in the second blood line branch,
    wherein each of the first and second membrane pumps comprises a pumping chamber and a flexible member separating the pumping chamber into a blood compartment and a working fluid compartment and being movable within the pumping chamber so as to vary the volume relationship between the blood compartment and the working fluid compartment, wherein the blood compartment is arranged for fluid communication with the upstream and downstream ends, and the working fluid compartment is arranged for fluid communication with the supply system, and wherein each of the first and second membrane pumps comprises an upstream valve and a downstream valve for controlling blood flow between the blood compartment and the upstream end and the downstream end, respectively, and wherein the disposable is configurable for operation in a first blood access mode, in which the blood withdrawal and blood return connectors are connected to a single access device, and the membrane pump arrangement is operable to alternately draw blood from the upstream end, and to pump blood through the downstream end, thereby generating a pulsatile flow of blood through the blood treatment unit, and in a second blood access mode, in which the blood withdrawal and blood return connectors are connected to a first and a second access device, respectively, and the membrane pump arrangement is operable to concurrently draw blood from the upstream end and pump blood through the downstream end, thereby generating an essentially continuous flow of blood through the blood treatment unit, wherein the membrane pump arrangement is configured for connection to the supply system such that alternating flows of treatment fluid generated by the supply system and supplied to the first and second membrane pumps causes the membrane pump arrangement to generate the pulsatile flow of blood in the first mode and the essentially continuous flow of blood in the second mode, and wherein one of the upstream or downstream valves is controllable to selectively open for blood flow by application of positive pressure to the treatment fluid, and (b) the other of the upstream or downstream valves is controllable to selectively block blood flow by application of positive pressure to the treatment fluid.

2. The apparatus of claim 1, wherein the disposable comprises a first line arrangement connected to the working fluid compartment, the upstream valve and the downstream valve of the first membrane pump, and a second line arrangement connected to the working fluid compartment, the upstream valve and the downstream valve of the second membrane pump, wherein the first and second line arrangements are configured for connection to the supply system.

3. The apparatus of claim 2, wherein the disposable is configurable for operation in the first blood access mode by the supply system via the alternating flows generating alternating positive and negative pressure in the treatment fluid in the first line arrangement while simultaneously generating alternating positive and negative pressure in the treatment fluid in the second line arrangement.

4. The apparatus of claim 2, wherein the disposable is configurable for operation in the second blood access mode by the supply system via the alternating flows generating alternating positive and negative pressure in the treatment fluid in the first line arrangement while simultaneously generating alternating negative and positive pressure in the treatment fluid in the second line arrangement.

5. A method of preparing the blood treatment apparatus of claim 2 for operation in one of a first blood access mode and a second blood access mode, the method comprising:

preparing the blood treatment apparatus for operation in the first blood access mode by configuring the supply system to generate alternating positive and negative pressure in the treatment fluid in the first line arrangement while simultaneously generating alternating positive and negative pressure in the treatment fluid in the second line arrangement, and preparing the blood treatment apparatus for operation in the second blood access mode by configuring the supply system to generate alternating positive and negative pressure in the treatment fluid in the first line arrangement while simultaneously generating alternating negative and positive pressure in the treatment fluid in the second line arrangement.

6. The apparatus of claim 1, wherein the supply system comprises a first fluid system for pumping the treatment fluid through the blood treatment unit during the blood treatment, and a second fluid system for supplying the alternating flows of treatment fluid to the membrane pump arrangement, wherein the first and second fluid systems are operated separately during the blood treatment.

7. The apparatus of claim 6, wherein the supply system comprises at least one priming valve which is operable to admit treatment fluid into the first and second fluid systems for filling all fluid lines in the first and second fluid systems with treatment fluid.

8. A method of preparing a blood treatment apparatus for operation in one of a first blood access mode and a second blood access mode, the apparatus comprising a supply system of a treatment fluid, and the method comprising:

obtaining a disposable comprising a blood treatment unit, a blood withdrawal connector connected to the blood treatment unit via a blood withdrawal line, and a blood return connector connected to the blood treatment unit via a blood return line, wherein one of the blood withdrawal line and the blood return line comprises a membrane pump arrangement operable to pump blood through the blood treatment unit, wherein the membrane pump arrangement comprises first and second blood line branches that are connected at an upstream end and at a downstream end, and wherein a first membrane pump is arranged in the first blood line branch, and a second membrane pump is arranged in the second blood line branch;

wherein the apparatus is configured for selective operation in the first blood access mode or the second blood access mode;

connecting the blood treatment unit to the supply system for generating a flow of the treatment fluid through the blood treatment unit;

if the apparatus is to be prepared for operation in the first blood access mode in which the blood withdrawal and blood return connectors are connected to a single access device, manipulating the disposable to block blood flow to and from the first membrane pump, and configuring the second membrane pump to alternately draw blood from the upstream end and pump blood through the downstream end, so as to generate a pulsatile flow of blood through the blood treatment unit; and if the apparatus is to be prepared for operation in the second blood access mode in which the blood withdrawal and blood return connectors are connected to a first and a second access device, respectively, configuring the first and second membrane pumps to concurrently draw blood from the upstream end and pump blood through the downstream end, so as to generate an essentially continuous flow of blood through the blood treatment unit.

9. The method of claim 8, further comprising, if the apparatus is to be operated in the first blood access mode, disabling the first membrane pump.

10. The method of claim 8, wherein each of the first and second membrane pumps comprises a pumping chamber and a flexible member separating the pumping chamber into a blood compartment and a working fluid compartment and being movable within the pumping chamber so as to vary the volume relationship between the blood compartment and the working fluid compartment, wherein the blood compartment is arranged for fluid communication with the upstream and downstream ends, and the working fluid compartment is arranged for fluid communication with the supply system, and wherein each of the first and second membrane pumps comprises an upstream valve and a downstream valve which are connected for fluid communication with the supply system and controllable to selectively block blood flow on generation of a positive pressure in the treatment fluid, said method further comprising:

connecting the disposable to the supply system for generating alternating flows of treatment fluid to the working fluid compartments of the first and second membrane pumps, and to the upstream and downstream valves, so as to cause the first and second membrane pumps to concurrently draw blood from the upstream end and pump blood through the downstream end.

11. The method of claim 10, further comprising, if the apparatus is to be operated in the first blood access mode, manipulating the disposable to block the flow of treatment fluid to and from the working fluid compartment of the first membrane pump.

12. An apparatus for blood treatment, the apparatus comprising:

a supply system of a treatment fluid; and a disposable configured for use in one of a first blood access mode and a second blood access mode during blood treatment, the disposable comprising a blood treatment unit for connection to the supply system that is operable to pump the treatment fluid through the blood treatment unit during the blood treatment, a blood withdrawal connector which is connected to the blood treatment unit via a blood withdrawal line, and a blood return connector which is connected to the blood treatment unit via a blood return line, wherein one of the blood withdrawal line and the blood return line comprises a membrane pump arrangement operable to pump blood through the blood treatment unit, wherein the membrane pump arrangement comprises first and second blood line branches that are connected at an upstream end and at a downstream end, wherein a first membrane pump is arranged in the first blood line branch, and a second membrane pump is arranged in the second blood line branch, wherein each of the first and second membrane pumps comprises a pumping chamber and a flexible member separating the pumping chamber into a blood compartment and a working fluid compartment and being movable within the pumping chamber so as to vary the volume relationship between the blood compartment and the working fluid compartment, wherein the blood compartment is arranged for fluid communication with the upstream and downstream ends, and the working fluid compartment is arranged for fluid communication with the supply system, and wherein each of the first and second membrane pumps comprises an upstream valve and a downstream valve which are connected for fluid communication with the supply system and controllable to selectively block blood flow on generation of a positive pressure in the treatment fluid; and control electronics programmed to: (i) for the first blood access mode direct the blood through only the second blood line branch, and (ii) for the second blood access mode direct the blood through the first blood line branch and the second blood line branch.

13. The apparatus of claim 12, wherein the disposable comprises a first line arrangement connected to the working fluid compartment of the first membrane pump, to the upstream valve of the first membrane pump and to the downstream valve of the second membrane pump, and a second line arrangement connected to the working fluid compartment of the second membrane pump, to the upstream valve of the second membrane pump and to the downstream valve of the first membrane pump, wherein the first and second line arrangements are configured for connection to the supply system, which is operable to generate alternating positive and negative pressure in the treatment fluid in the first line arrangement while simultaneously generating alternating negative and positive pressure in the treatment fluid in the second line arrangement.

* * * * *